United States Patent [19]
Gordon et al.

[11] Patent Number: 5,439,100
[45] Date of Patent: Aug. 8, 1995

[54] PACKAGING SYSTEM FOR DISPENSING CARTRIDGE FOR VOLATILES

[75] Inventors: Andrew D. Gordon, Cincinnati, Ohio; Daniel E. Linkugel, Cold Spring, Ky.

[73] Assignee: The Dial Corp., Phoenix, Ariz.

[21] Appl. No.: 57,083

[22] Filed: May 4, 1993

[51] Int. Cl.$^6$ ............................................. F17C 13/00
[52] U.S. Cl. ........................................ 206/0.5; 206/204; 206/461; 239/56; 239/60
[58] Field of Search ............ 206/0.5, 204, 213.1, 206/461, 467, 469, 471; 239/54, 55, 56, 60

[56] References Cited

U.S. PATENT DOCUMENTS

| | | |
|---|---|---|
| 3,310,235 | 3/1967 | Zbinden . |
| 3,358,821 | 12/1967 | Weisberg . |
| 3,951,622 | 4/1976 | Wilk . |
| 4,055,672 | 10/1977 | Hirsh et al. . |
| 4,130,245 | 12/1978 | Bryson . |
| 4,145,001 | 3/1979 | Weyenberg et al. . |
| 4,157,787 | 6/1979 | Schwartz . |
| 4,161,283 | 7/1979 | Hyman . |
| 4,176,567 | 12/1979 | Weisberg . |
| 4,240,552 | 12/1980 | Brown .................. 206/461 |
| 4,248,380 | 2/1981 | Lee et al. . |
| 4,254,910 | 3/1981 | Martin . |
| 4,356,969 | 11/1982 | Obermayer et al. . |
| 4,387,849 | 6/1983 | Van Loveron et al. . |
| 4,445,641 | 5/1984 | Baker et al. . |
| 4,634,614 | 1/1987 | Holzner . |
| 4,745,007 | 5/1988 | Addamiano et al. . |
| 4,849,606 | 7/1989 | Martens, III et al. . |

FOREIGN PATENT DOCUMENTS

| | | |
|---|---|---|
| 0359820 | 3/1990 | European Pat. Off. . |
| 0488323 | 6/1992 | European Pat. Off. . |
| 2642726 | 8/1990 | France . |
| 294768 | 7/1980 | Germany ............... 206/204 |
| 446178 | 10/1967 | Switzerland . |

OTHER PUBLICATIONS

International Search Report (PCT/US93/04162), Drackett Brands, Inc. (Gordon et al.), Feb. 7, 1994.

Primary Examiner—David T. Fidei
Attorney, Agent, or Firm—Frost & Jacobs

[57] ABSTRACT

A protective package system for containing a delivery cartridge for volatile substances such as fragrances, deodorizers, air fresheners and the like, wherein the cartridge includes an active ingredient reservoir with a permeable surface through which substances may move from the reservoir. The packaging system preferably includes a cartridge container having a storage area for receiving the cartridge, and a substantially open top with an outer periphery. A peelable lid is sealingly attached to the outer periphery of the container, and a blotter is attached to at least a portion of the inner surface of the peelable lid and preferably spaced inwardly from the outer edge of the lid so as not to interfere with the sealing attachment of the lid to the container. The blotter is thereby held in face-to-face contact with the permeable surface of the cartridge within the packaging system when the lid is in sealed condition and remains captively attached to the lid upon opening of the packaging system. In a preferred embodiment, the container is further provided with a blotter recess to facilitate preliminary alignment of the blotter with the permeable membrane of a cartridge held therewithin, and to facilitate captive attachment of the blotter to the inner surface of the peelable lid during sealing procedures. In this way, the blotter can be independently placed within an open container after the volatile cartridge has been loaded with its permeable membrane facing outwardly through the open top. Manufacturing procedures are thereby simplified, yet the blotter will be captively attached to the peelable lid to minimize potential for contact with the user upon opening.

13 Claims, 2 Drawing Sheets

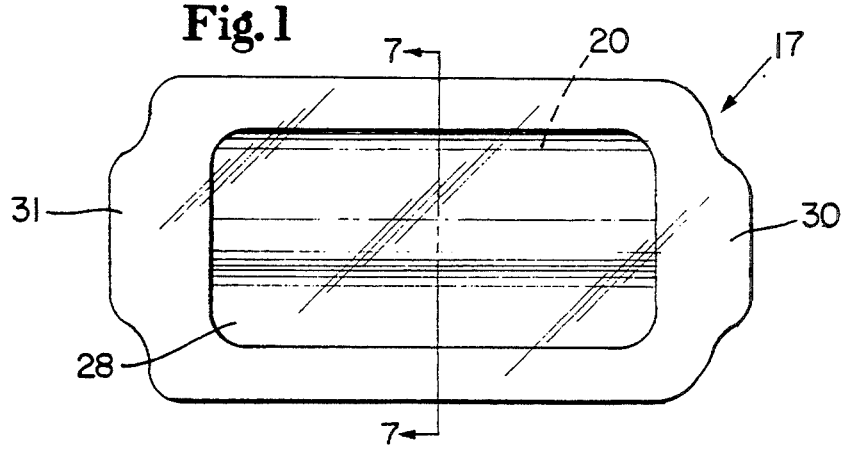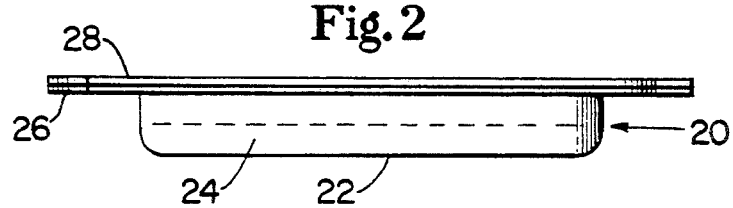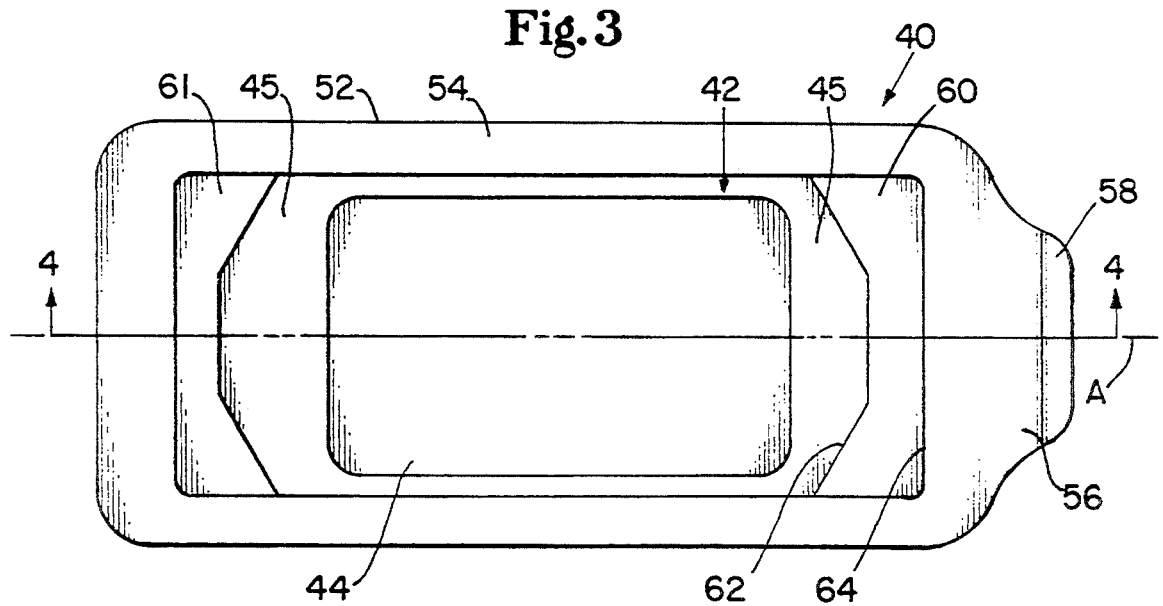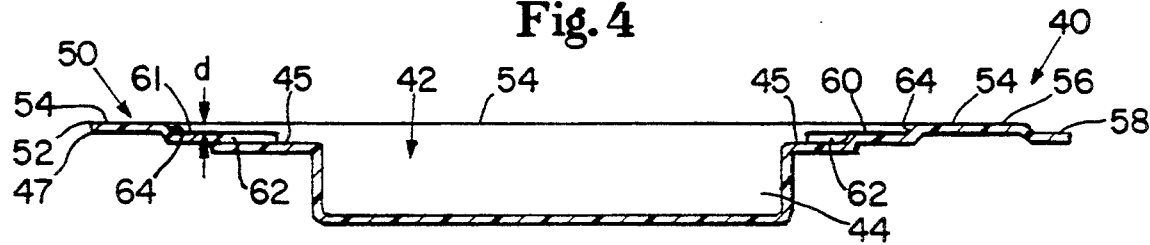

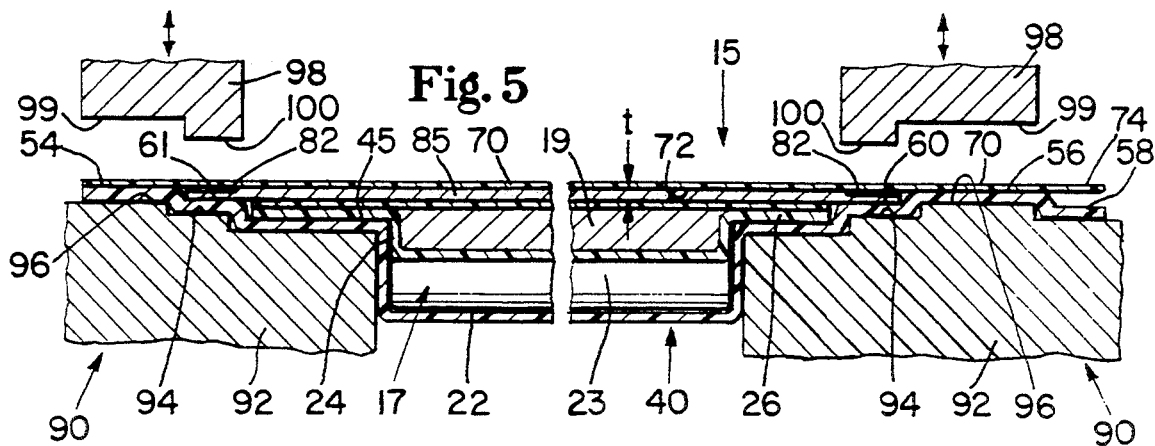
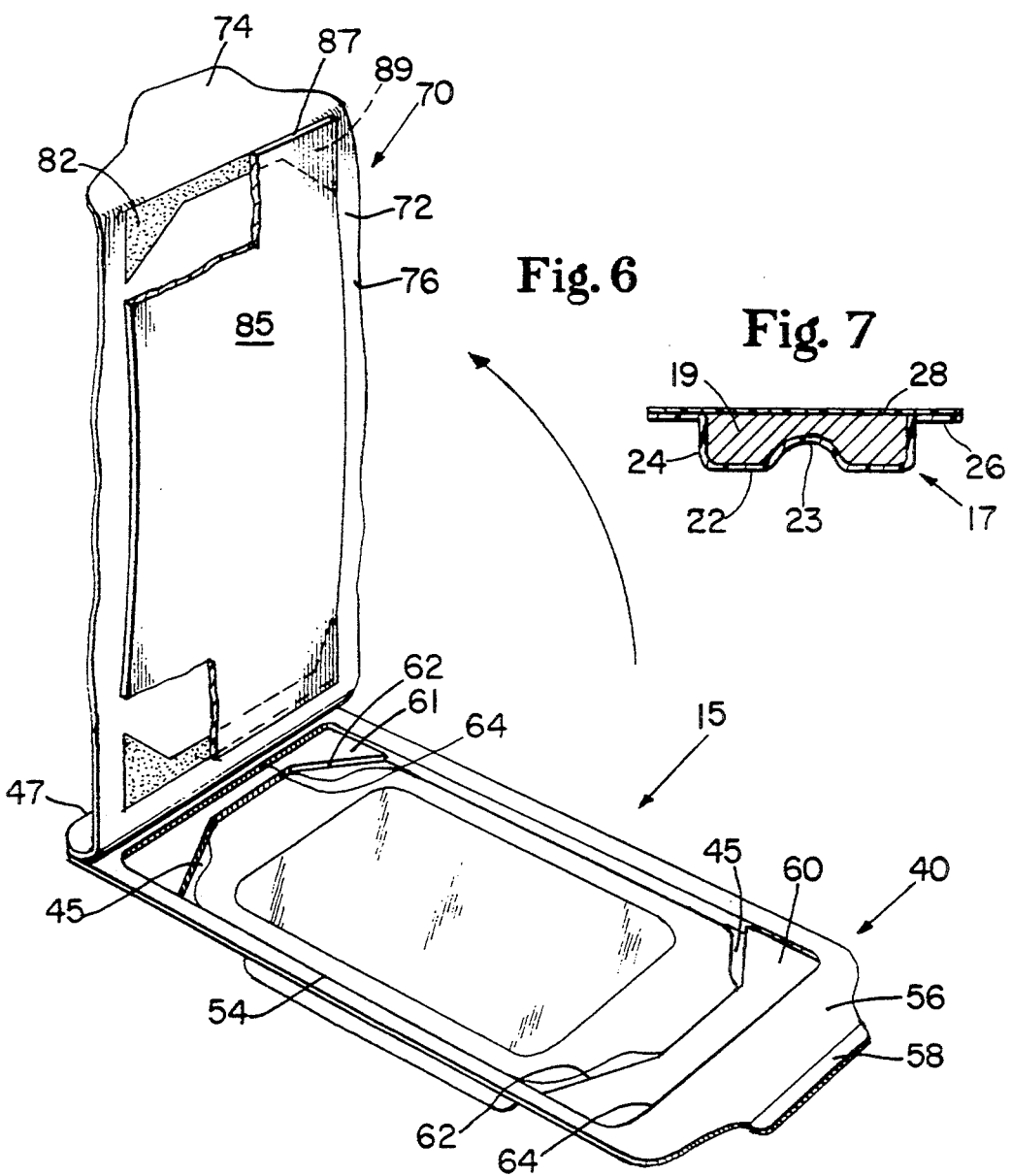

PACKAGING SYSTEM FOR DISPENSING CARTRIDGE FOR VOLATILES

TECHNICAL FIELD

This invention relates to a packaging system for dispensing cartridges for volatile substances such as fragrances, deodorizers, air fresheners, and the like, which include at least one permeable surface through which the volatile substance is released from the cartridge in use, and, more particularly, to an improved protective package system for containing the delivery cartridge for volatile substances in a storage stable manner and including a blotter mechanism for absorbing and retaining undesirable migration of the volatile material through the permeable surface, with that blotter being captively attached to the package after opening.

BACKGROUND ART

The utilization of volatile substances for air fresheners, fragrances, and other air-treating dispensing applications is relatively wide-spread and provided in a number of structural arrangements. As described in U.S. Pat. No. 4,157,787, which is issued to B. Schwartz, a number of air-freshening type dispensing products comprise a quantity of air-treating material, which, when exposed to the atmosphere, is to release its active substances in a predetermined, controlled manner in the form of vapor. Consequently, during the period of time in which these products are not in use (e.g. during shipping, storage, etc.), it is desirable to prevent the vaporization of the active substances to prevent premature release of the fragrance or other air-treating active substances. Conventionally, the dispenser itself is sealed with a cover layer of nonporous material to prevent vaporization of the active substances. The Schwartz air freshener dispenser is described as including a porous layer which covers the opening of the dispenser and underlies a removable, non-porous seal or cover layer. Removal of the non-porous layer enables permeation and vaporization to begin.

U.S. Pat. No. 4,130,245, which issued to J. Bryson, discloses a liquid dispensing package designed to provide a more uniform dispensing rate by maintaining maximum surface contact between the volatile substance held therewithin and the interior surfaces of the package. The Bryson device incorporates an outer porous layer superposed over a heat-sealable plastic layer to assist in heat-sealing manufacturing procedures. Bryson does not specifically provide any particular packaging system for its dispensing device. Another vapor-type dispensing product is shown in U.S. Pat. No. 4,356,969, which issued to A. Obermayer et al. While this dispensing device contemplates utilization of a macroporous overlay sheath material to control the rate of evaporation of its volatile substances, additional packaging not included in this patent would be necessary to enclose this dispenser for transportation and storage.

Another device for treating ambient air is set forth in U.S. Pat. No. 4,634,614, which issued to G. Holzner. The Holzner device includes an active substance containing chamber, a permeable wall covering that chamber, a thin paper layer attached to the outer surface of the permeable wall, and a polymeric material having a sheet of protective impermeable material such as metal foil attached to the outer surface of the paper. The impermeable material prevents migration of active substances and vaporization, and the paper layer enables detachment of the polymeric and impermeable material from the permeable wall when dispensing is desired. Particularly, the paper layer tears away from the permeable wall, allowing permeation and vaporization to begin. A somewhat similar device is shown in U.S. Pat. No. 4,161,283, which issued to S. Hyman. The Hyman device includes a pouch or envelope defined by an outer wall including a first barrier layer which is impermeable to diffusion, and an inner polymer diffusion layer. When use of the device is desired, the outer barrier layer is removed, and diffusion and vaporization is thereby enabled through the polymeric diffusion layer.

A somewhat related device is shown in U.S. Pat. No. 4,055,672, which issued to A. Hirsch et al. In this reference, a pre-formed tray has heat-sealable flanges to which a composite lid is sealingly attached. The lid includes an inner layer of highly gas permeable material, an outer layer which is substantially gas impermeable, and a central adhesive layer which has a strength lower than the cohesive strength of the inner layer. When permeation from the package is desired, the outer layer is peeled away from the inner layer and along with the adhesive layer for removal from the package.

The Weyenberg et al. package shown in U.S. Pat. No. 4,145,001 similarly includes a multi-layer laminate having an outer layer impermeable to the contained substance and its vapors, with the outer layer being adhered to an inner permeable layer. These inner and outer layers are connected by a release layer which enables selective removal of the outer impermeable layer to commence permeation and vaporization of the active substances. Application of a package as described in the Weinberg et al. patent is shown in the later U.S. Pat. No. 4,849,606, which issued to E. Martens et al. In the Martens reference, a container for active substances is provided with a peripheral flange to which the multi-layer laminate as described in Weinberg et al. is sealed. The resulting tamper-resistant container is described as appropriate for use with air freshening substances and the like in conjunction with an electrically heated vapor dispensing apparatus. When air freshening is desired, the impermeable layer of the container is removed to expose the permeable layer for dispensing procedures.

While it is clear that there are a number of prior dispensing and packaging structures which incorporate the use of specially designed plural laminates which enable selective removal of an impermeable protective layer from a permeable membrane or cover of a dispensing cartridge, these relatively complex laminate structures are not always feasibly available or desired for all applications. On the other hand, packages for containing cartridges of volatile substances having a permeable surface must be able to contain such substances so as to prevent the premature consumption of the volatile or active substance, and to prevent undesirable contact by the user with various oils and other substances which can move through the permeable surface. A simple yet reliable packaging system for containing volatile cartridges with a permeable membrane was needed and has heretofore been unavailable in the industry.

DISCLOSURE OF THE INVENTION

It is an object of this invention to address the above-mentioned problems and shortcomings of the packaging systems and laminate products heretofore available in the industry.

It is another object of the present invention to provide an improved packaging system for dispensing cartridges for volatile substances which prevents premature consumption of the volatiles while maintaining reliable and hygienic storage thereof.

It is also an object of the present invention to provide a simplified packaging system for dispensing cartridges for volatiles having a permeable membrane or cover through which oils and/or other substances can predictably migrate, with such packaging system providing reliable control of such substances.

It is yet another object of the present invention to provide an improved packaging system for volatile substance dispensing cartridges which includes a blotter member connected to the package to control substances which may migrate through the permeable membrane during shipping and storage, and which maintains in a collective substances substantially out of contact with the user.

In accordance with one aspect of the present invention, there is provided a protective package system for containing a delivery cartridge for volatile substances such as fragrances, deodorizers, air fresheners and the like, wherein the cartridge includes an active ingredient reservoir with a permeable surface through which substances may move from the reservoir. The packaging system preferably includes a cartridge container having a storage area for receiving the cartridge, and a substantially open top with an outer periphery. A peelable lid with an inner surface and an outer edge can be sealingly attached to the outer periphery of the container, whereby the lid is peeled away from at least a portion of the outer periphery during opening procedures. A blotter is captively attached to at least a portion of the inner surface of the peelable lid and spaced inwardly from the outer edge of the lid so as not to interfere with the sealing attachment of the lid to the container. The blotter is thereby held in face-to-face contact with the permeable surface of the cartridge confined within the packaging system when the lid is in sealed condition and remains attached to the lid upon opening of the packaging system.

In a preferred embodiment, the container is further provided with a blotter recess to facilitate preliminary alignment of the blotter with the permeable membrane of a cartridge held therewithin, and to facilitate captive attachment of the blotter to the inner surface of the peelable lid during sealing procedures. In this way, the blotter can be independently placed within an open container once the volatile cartridge has been loaded therewithin with its permeable membrane facing outwardly through the open top. Manufacturing procedures are thereby simplified, yet the blotter will be captively attached to the peelable lid to minimize potential for contact with the user upon opening.

BRIEF DESCRIPTION OF THE DRAWINGS

While the specification concludes with claims particularly pointing out and distinctly claiming the present invention, it is believed the same will be better understood from the following description taken in conjunction with accompanying drawings in which:

FIG. 1 is a top plan view of an exemplary cartridge insert for a volatile delivery system;

FIG. 2 is a side elevational view of the cartridge of FIG. 1;

FIG. 3 is a top plan view of a preferred embodiment of a cartridge container of a packaging system made in accordance with the present invention;

FIG. 4 is a vertical cross-sectional view of the container of FIG. 3, taken along line 4—4 thereof;

FIG. 5 is an enlarged, partial cross-sectional view of a preferred embodiment of a protective packaging system made in accordance with the present invention, shown in sealed condition and as supported by a tooling for sealing the lid to the container;

FIG. 6 is a perspective view of the packaging system of FIG. 5, illustrated after the lid has been peeled to open condition for access to the cartridge therewithin; and FIG. 7 is a vertical cross-sectional view of the dispensing cartridge of FIG. 1, taken along line 7—7 thereof.

DETAILED DESCRIPTION OF THE INVENTION

Referring now to the drawings in detail, wherein like numerals indicate the same elements throughout the views, FIGS. 1, 2 and 7 illustrate an exemplary cartridge or insert 17 for a volatile substance delivery system. As mentioned above, such a volatile delivery system might preferably be an air freshening device or other atmosphere conditioning apparatus for releasing various active substances and ingredients to the ambient atmosphere via vaporization. FIGS. 3 and 4 illustrate a preferred cartridge container 40 for receiving and supporting a volatile delivery cartridge, while FIG. 5 illustrates a preferred embodiment of an overall packaging system 15 made in accordance with this invention and sealed with a cartridge inside. FIG. 6 illustrates the open condition of a packaging system 15.

As shown in FIGS. 1, 2 and 7, an air freshening dispensing cartridge or insert 17 is illustrated as including a pan-shaped active ingredient reservoir 20 generally defined by a bottom wall 22 and upstanding peripheral side and end walls 24. Bottom wall 22 is illustrated as including a central longitudinal recess (26) as best seen in FIG. 7. An upper edge or flange 26 surmounts side walls/end walls 24 to provide a convenient sealing surface upon which a permeable delivery surface 28 (e.g., a permeable or perforated membrane) may be provided. In a preferred embodiment, the reservoir 20 is provided as a laminate structure designed to adequately maintain a mixture of air-treating chemicals and/or active ingredients (e.g., gel or liquid 19).

Particularly, it is preferred that the reservoir 20 be substantially impervious to migration, permeation, absorption or other movement of the volatile substance, and, of course, inert to that substance. For example, a preferred laminate might include a low density polyethylene inner layer joined to an outer layer of acrylonitrile polymer (as known as Barex). These layers form an effective barrier which is substantially impermeable to the fragrance or other substances to be held within the container. The polyethylene and Barex layers can be joined to one another by any compatible adhesive, and the resulting laminate is preferably formed into its cup-like flanged form by a conventional punch, vacuum forming, or similar tray forming tool.

Delivery surface 28 is preferably provided in the form of a permeable membrane or cover, and might preferably comprise a co-polymer membrane formed from polyethylene and vinyl acetate. Upper edges 26 of the side walls may also include an oppositely disposed pair of end tabs 30 and 31 to facilitate handling and manufacturing procedures. The size and shape of the permeable surface 28 substantially corresponds with the shape and size of upper edge 26 of reservoir 20 to facilitate heat sealing or similar attachment to reservoir 20 once the volatile substance (e.g., 19) is filled within reservoir 20.

The packaging system 15 of the present invention further comprises a container or blister 40 designed for receiving and holding a delivery cartridge (e.g., 17), as will be described. As best seen in FIGS. 3 and 4, cartridge container 40 preferably comprises a storage area 42 which includes a substantially centrally located reservoir recess 44. As can be appreciated from the vertical cross-sectional view of FIG. 4, container 40 has an overall cup-shaped appearance, wherein storage area 42 is preferably specifically designed to closely correspond in size and shape to a cartridge 17 to be held therewithin. Reservoir recess 44 is designed to receive and accommodate ingredient reservoir 20 of a cartridge 17, while the balance of storage area 42 correspondingly receives and supports the upper portions of cartridge 17, including upper edges 26 and oppositely disposed end tabs 30 and 31. Particularly, tab recesses 45 respectively receive end tabs 30 and 31 in a somewhat loose fitting arrangement.

Cartridge container 40 comprises a substantially open top 50 defined by an outer periphery 52 and a flat peripheral flange member 54 circumscribing storage area 42. While container cartridge 40 is illustrated in a preferred embodiment as generally symmetrical about its longitudinal axis A, it is preferred to provide an extended tab portion 56 adjacent one longitudinal end of container 40, with extended tab 56 including a slightly recessed peel tip 58. As will be understood, extended tab 56 and its accompanying peel tip 58 ensure that a portion of the peelable lid (e.g., 70) of packaging system 15 will remain at least partially unattached to the container and readily available for facilitating opening procedures. It will be understood that the symmetry about longitudinal axis A is not critical, and that the overall conformations of the cartridge and its container can be provided in any of a variety of forms.

As best seen in FIGS. 3 and 4, container 40 also preferably comprises a pair of oppositely disposed blotter recesses 60 and 61, spaced along longitudinal axis A. The areas defined by recesses 60 and 61 are located inwardly within the peripheral flange 54, and longitudinally spaced at least partially outside of storage area 42. It is contemplated that cartridge container 40 will preferably be provided in the form of a substantially transparent polymer material, such as polyethylene teraphthalate (PET, e.g. grade 9921) which can be thermo formed into any of a variety of relatively intricate shapes. As illustrated in the figures, container 40 is preferably drawn into a unitary cup-shaped structure, wherein the reservoir and tab recesses 44 and 45 generally correspond with the shape and size of a cartridge or insert 17 to be held therewithin.

While recessed relative to the outer peripheral flange 54, blotter recesses 60 and 61 are less deep than the adjacent tab recesses 45. The recess embosses 62 define oppositely disposed, substantially flared rectangular areas of recesses 60 and 61 located longitudinally within peripheral flange 54, and longitudinally outside of storage area 42. As will be seen, recesses 60 and 61 provide for preliminary alignment of a blotter (e.g., 85), such that the blotter is located substantially within container 40, while maintaining a substantially unimpeded peripheral area (e.g., along flange 54) for reliably sealing container 40. The areas of recesses 60 and 61 are defined by the respective recess embosses 62 and the inner edge 64 of flange 54.

As best illustrated in FIGS. 5 and 6, a peelable flexible lid 70 is provided to overlie container 40 and its contents, and to provide a substantially impermeable barrier to the open top 50 thereof. In this regard, it is preferred that lid 70 be provided in the form of a flexible laminate structure combining, for example, an impermeable layer such as metal foil, and polyethylene. While any impermeable material could be utilized for lid 70, the flexible laminate structure described herein is preferred for optimum performance and manufacturing considerations. Peelable lid 70 further comprises an inner surface 72 including an outer peripheral edge 76, and a peel tab or extended section 74 at one longitudinal end.

As mentioned above, dispensing cartridges for volatile substances which include permeable delivery surfaces can experience permeation or movement of the active materials or other substances held therewithin at any time following the manufacturing procedures. It is also known that some of the active ingredients in these products can be irritating, if any substantial contact is experienced by the user. While some of the packaging structures described above minimize the permeation and other movement of such substances through membranes and the like by intimately sealing a barrier layer over the permeable layers, packaging which does not include direct sealing of a barrier layer over permeable layers will experience some migration and/or condensation as a result of materials escaping therethrough. For example, in the embodiment of the cartridge 17 described above, fragrances, oils, or the like may indeed permeate through membrane or cover 28 during transportation and storage procedures.

It has been found that inclusion of an absorbent or blotter-type structure within the packaging system is a preferred means for controlling the small amounts of migrating substances. In packaging system 15 of the present invention, a blotter 85 is inserted within packaging system 15 once cartridge 17 has been placed within container 40. As illustrated in FIGS. 5 and 6, the outer shape and size (e.g., 87) of blotter 85 is preferably limited such that while a substantial portion of (and preferably the entire) permeable surface 28 of insert 17 is covered when the packaging system 15 is sealed, the outer edge (e.g., 87) of blotter 85 does not interfere with the peripheral seal between lid 70 and container 40. While it is contemplated that absorbent blotter 85 may comprise any of a variety of materials, having a relatively high affinity for substances such as oil or actives which may condense within packaging system 15 and/or permeate through surface 28, an acid bleached cellulose blotter material (such as available from Orlandi, of Farmingdale, N.Y.) is useful in air-freshener applications.

It has further been found that while use of a blotter overcomes the problems associated with condensation and/or collection of permeating substances within packaging system 15, it is preferred that the structure of packaging system 15 further provide control of blotter 85 upon opening procedures. In this way, the packaging materials are most efficiently disposed of, while chance for contact by the user with substances absorbed by blotter 85 is minimized. Consequently, it is preferred that blotter 85 be captively attached to cartridge container 40, so that upon opening of lid 70, the blotter does not interfere with access to the cartridge 17 held therewithin, nor is direct contact with or manipulation of blotter 85 by the user required.

As best seen in FIGS. 5 and 6 it is preferred that blotter 85 be at least partially attached to lid 70, such as at captive attachment points 89. As will be appreciated, while blotter 85 could be attached to lid structure 70 prior to placement of the lid on a container 40, it is preferred that the blotter be independently provided to container 40 after cartridge 17 is placed therewithin, and prior to alignment and sealing of the lid 70. In this way, precise alignment procedures which would be required for lids already having blotters attached are obviated. However, such an arrangement provides a problem for achieving the captive attachment of the blotter to the lid, as many delivery cartridges 17 are at least partially flexible and can provide little in the way of support for pressure-type attachment arrangements. As can be appreciated from consideration of FIGS. 5 and 6, once a partially flexible cartridge 17 is placed within storage area 42, the flexible nature of cartridge 17 and its liquid or gel-like active substances cannot (and should not be used to) provide adequate resistance for undertaking reliable pressure-type attachment procedures.

FIG. 5 illustrates, in schematic form, a tooling fixture or template arrangement 90 for sealing the lid 70 to container 40 and for providing captive attachment of blotter 85 to lid 70 (and/or directly to container 40). Particularly, tooling 90 at least one fixture 92 with relieved lands on upper surface, such as blotter recess land 94 and the peripheral seal support land 96. A sealing platen (e.g., 98) is utilized to impose sealing/attachment pressure via surface 99 against the upper surface of lid 70, urging lid 70 into sealing engagement with flange 54, and pressing the inner surface 72 of lid 70 into at least intermittent attachment with blotter 85 (as indicated at attachment areas 82) via the appropriately extended surface 100 of platen 98. Platen 98 may preferably be heated where heat activated adhesives are used and/or welding attachment is desired. In this regard, the shape and effective area of attachment areas 82 will be generally defined and limited by the corresponding blotter recesses 60 and 61 and shape of extended surface 100. Particularly, it has been found that to ensure reliable captive attachment of blotter 85 to container 40 (and the inner surface of lid 70), a minimum of approximately 8% of the surface area of blotter 85 should be adhesively joined to the inner surface of lid 70. While this percentage may vary for different combinations of materials used for blotter 85 and the inner surface of lid 70, this minimum attachment area has been found to be quite effective for ensuring adequate connection and continued captivity.

As will be understood, tooling 90 and platen 98 may be provided in the form of sequential and separate pressing arrangements, or, as illustrated, may preferably be combined in a single tool and simultaneous sealing arrangement. As can also be appreciated from FIGS. 4 and 5, blotter recesses 60, 61 have a predetermined depth (d) which is designed to allow for alignment of blotter 85 such that the blotter is located substantially within container 40, while maintaining a substantially unimpeded peripheral area (e.g., along flange 54) for reliably sealing container 40. In this way, upon sealing lid 70 to cartridge container 40, blotter 85 will necessarily be slightly compressed therewithin between surface 100 and surface 94 of tooling 90, thereby facilitating a reliable attachment between blotter 85 and surface 72 in areas 82 and ensuring that blotter 85 will be held in substantially intimate face-to-face arrangement with permeable surface 28 in closed condition, as described above.

Implementation of the present improved packaging system would preferably include providing a delivery cartridge or insert (e.g., 17) as described herein for insertion into a cartridge container formed in accordance with the description set forth above. Particularly, the cartridge is to be inserted into the storage area of the container with its permeable surface oriented upwardly and towards the open end or top of the container. Next, a blotter is preferably located at least partially within the container and on top of the cartridge held therewithin, such that the blotter is substantially aligned with and surmounts the permeable surface of the cartridge. As indicated, the blotter is sized and aligned so as not to substantially interfere with the peripheral seal of the container by a lid structure.

It should be noted, however, that an alternative of captively attaching the blotter to the container would be to allow at least some overlap of the blotter onto the peripheral sealing flange (e.g., 54) at one longitudinal end of the container (e.g., back end 47 for the container seen in FIGS. 4 and 6). If the blotter were attached adjacent one longitudinal end in this way, it would also be preferred to connect the other longitudinal end of the blotter to the inside surface of the lid to prevent interference with removal of the dispensing cartridge from the container. This alternative would not be preferred where it is likely that the lid will be completely removed from the container upon opening, as the blotter might adhere to the container and/or be at least partially separated from the lid.

Once the blotter is arranged on top of the permeable surface of the cartridge, a lid having impermeable features is provided and then sealed to the peripheral flange of the container. It is preferred that substantially simultaneously with the sealing of the lid to the container, the blotter will be captively attached to the inner surface of the lid so as not to interfere with the sealing arrangement, and so as to be held in face-to-face contact with the permeable surface. In this way, the blotter will remain attached to the container and lid upon opening of the packaging system. It will also be understood that this packaging system is quite amenable to high speed, relatively standard, form, fill and seal operations and equipment.

Having shown and described the preferred embodiments of the present invention, further adaptions of the improved packaging system of the present invention can be accomplished by appropriate modifications by one of ordinary skill in the art without departing from the scope of the present invention. Several of such potential modifications have been mentioned, and others will be apparent to those skilled in the art. Accordingly, the scope of the present invention should be considered in terms of the following claims and is understood not to be limited to the details of structure and operation shown and described in the specification and drawings.

We claim:

1. A protective packaging system for containing a delivery cartridge for volatile substances such as fragrances, deodorizers, and other air treatment materials, wherein the delivery cartridge includes an active ingredient reservoir with a permeable surface through which substances may move from the reservoir, said packaging system comprising:
  (a) an outer cartridge container having a storage area for receiving said delivery cartridge, and a substantially open top with an outer periphery, said outer cartridge container including a peelable lid having an inner surface and an outer edge which can be attached to said outer periphery to sealing close said outer cartridge container, said lid being peeled away from at least a portion of said outer periphery during opening procedures; and
  (b) a blotter independently received within said outer cartridge container, said blotter being interposed between said peelable lid of the outer cartridge container and the permeable surface of the delivery cartridge, and said blotter being held in face to face contact with said permeable surface of the delivery cartridge within said packaging system when said lid is in sealed condition.

2. The packaging system of claim 1, wherein said blotter is captively attached to at least a portion of said cartridge container and remains attached to said container upon opening of said system.

3. The packaging system of claim 1, further comprising a recess formed adjacent said open top of said container to receive and facilitate alignment of said blotter adjacent to the permeable surface of a delivery cartridge received within said container, and wherein said blotter is spaced inwardly from said outer edge of said lid such that it does not interfere with the sealing attachment of said lid to said outer periphery of the container.

4. The packaging system of claim 3, wherein said container comprises a peripheral flange adjacent said outer periphery, and wherein said recess is located inwardly from said outer periphery and adjacent said flange, said recess having an effective shape and size which substantially corresponds to said blotter.

5. The packaging system of claim 3, wherein said storage area of said container comprises at least one cavity within the outer periphery for receiving and holding a cartridge, and said recess is located within said outer periphery between said storage area and said flange to provide a plurality of spaced lands which support said blotter adjacent said lid during sealing procedures.

6. The packaging system of claim 1, wherein said container comprises a substantially longitudinal axis along a predetermined length, and wherein a pair of lands are provided on said container in spaced relationship along said longitudinal axis for facilitating captive attachment of said blotter at a pair of longitudinally spaced points on said lid.

7. The packaging system of claim 1, wherein at least a portion of said cartridge to be received within said storage area is partially flexible and cannot support substantial external pressure for sealing procedures, said lid being sealed to said outer periphery, and said blotter being captively attached to said lid at one or more positions located radially outside of said storage area and the flexible portion of said cartridge.

8. A protective packaging system for containing an at least partially flexible delivery cartridge for volatile substances such as fragrances, deodorizers, and other air treatment materials, wherein the delivery cartridge includes an active ingredient reservoir with a permeable surface through which substance may move from the reservoir, said packaging system comprising:
  (a) an outer cartridge container having a storage area for receiving said delivery cartridge, a substantially open top with an outer periphery, and a peripheral flange adjacent said outer periphery, said outer cartridge container including a peelable lid having an inner surface and an outer edge which can be sealing attached to said flange of said outer cartridge container to close said outer cartridge container, said lid being peeled away from at least a portion of said outer periphery during opening procedures; and
  (b) a blotter having an outer shape and being captively attached to at least a portion of said inner surface of said peelable lid, a substantial part of said outer shape being spaced inwardly from said outer edge of said lid such that it does not interfere with the sealing attachment of said lid to said flange of the outer cartridge container, said blotter being interposed between said peelable lid of the outer cartridge container and the permeable surface of the delivery cartridge, and said blotter being held in face to face contact with said permeable surface of the delivery cartridge within said packaging system when said lid is in sealed condition and remaining attached to said lid upon opening of said system.

9. The packaging system of claim 8, further comprising a recess formed adjacent said open top of said container to receive and facilitate alignment of said blotter adjacent to the permeable surface of a delivery cartridge received within said container.

10. The packaging system of claim 9, wherein said outer shape of the container comprises a peripheral flange adjacent said outer periphery, and wherein said recess is located inwardly from said outer periphery and adjacent said flange, said recess having an effective shape and size which substantially corresponds to said outer shape of the blotter.

11. The packaging system of claim 9, wherein said storage area of said container comprises at least one cavity within the outer periphery for receiving and holding a cartridge, and said recess is located within said outer periphery between said storage area and said flange to provide a plurality of spaced lands which support said blotter adjacent said lid during sealing procedures.

12. The packaging system of claim 8, wherein said container comprises a substantially longitudinal axis along a predetermined length, and wherein a pair of lands are provided on said container in spaced relationship along said longitudinal axis for facilitating captive attachment of said blotter at a pair of longitudinally spaced points along said lid.

13. The packaging system of claim 8, wherein said lid is sealed to said flange and said blotter being captively attached to said lid at a plurality of positions spaced radially outside of said storage area and the flexible portion of said cartridge.

* * * * *